United States Patent [19]

Balis

[11] Patent Number: 5,627,161

[45] Date of Patent: May 6, 1997

[54] METHOD FOR TREATING TUMORS WITH UDPG

[75] Inventor: M. Earl Balis, New York, N.Y.

[73] Assignee: Memorial Hospital for Cancer and Allied Diseases, New York, N.Y.

[21] Appl. No.: 27,547

[22] Filed: Mar. 8, 1993

Related U.S. Application Data

[63] Continuation of Ser. No. 921,357, Jul. 27, 1992, abandoned, which is a continuation of Ser. No. 570,206, Jul. 17, 1990, abandoned, which is a continuation of Ser. No. 802,519, Nov. 27, 1985, abandoned, which is a continuation-in-part of Ser. No. 683,873, Dec. 20, 1984, abandoned.

[51] Int. Cl.$^6$ .................. A61K 31/70; A61K 31/505; A61K 31/52

[52] U.S. Cl. .................. 514/51; 514/256; 514/261; 514/262

[58] Field of Search .................. 514/51, 256, 261, 514/262

[56] References Cited

U.S. PATENT DOCUMENTS

| | | | |
|---|---|---|---|
| 3,717,547 | 2/1973 | Nakayama et al. | 435/90 |
| 3,787,392 | 1/1974 | Ulrich et al. | 536/27 |
| 3,803,125 | 4/1974 | Ulrich et al. | 536/27 |

OTHER PUBLICATIONS

Chiesara et al Chem Abst. 94:58307n, 1981.
Klohs et al., Journal of Cellular Phsyology, vol. 119, Apr. (1984), pp. 23–28.
Shur et al., Developmental Biology, vol. 73, (1979), pp. 178–181.
Keppler, Cancer Research, vol. 37, Mar. (1977), pp. 911–917.
Krug et al., Biochem. Journal, vol. 217, (1984), pp. 701–708.
Roussett et al., Cancer Research, vol. 44, No. 1, Jan. (1984), pp. 154–160.
Weckbecker et al., Biochemical Pharmacology, vol. 33, No. 14, (1984), pp. 2291–2298.
Granzow et al., The Journal Of Cell Biology, vol. 89, Jun. (1981), pp. 475–484.
Keppler et al., Adv. Enzyme Regul., vol. 23, (1985), pp. 61–79.
Keppler et al., Adv. Enzyme Regul., vol. 24, (1985), pp. 417–424.

*Primary Examiner*—John W. Rollins
*Attorney, Agent, or Firm*—John P. White

[57] ABSTRACT

UDPG shows tumor-specific inhibition of PRPP and this suggests that this action might prove to be useful in combination therapy with inhibitors of purine and pyrimidine nucleotide synthesis in various rescue regimens. High levels of PRPP in tumors were greatly affected by treatment with UDPG.

1 Claim, 1 Drawing Sheet

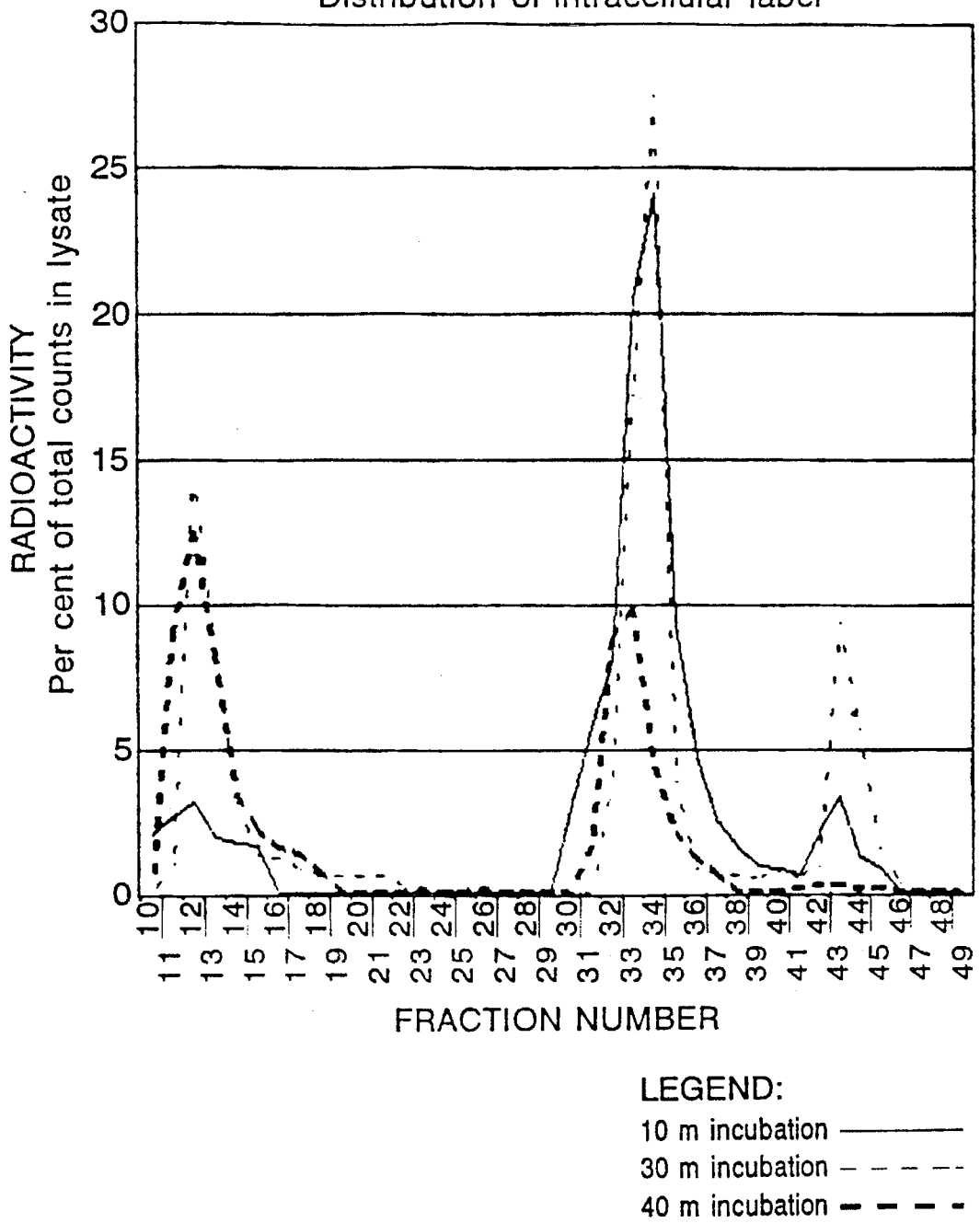

METHOD FOR TREATING TUMORS WITH UDPG

This application is a continuation of U.S. Ser. No. 921,357, filed Jul. 27, 1992, now abandoned, which is a continuation of U.S. Ser. No. 570,206, filed Jul. 17, 1990, now abandoned, which is a continuation of U.S. Ser. No. 802,519, filed Nov. 27, 1985, abandoned, which is a continuation-in-part of U.S. Ser. No. 683,873, filed Dec. 20, 1984, now abandoned.

BACKGROUND OF THE INVENTION

The UDPG (uridine-diphosphoglucose) composition has been known for some time. It has been in use in Italy for 20 years. Methods for its synthesis are disclosed. U.S. Pat. No. 3,787,392 issued to Bergmeyer et al. shows synthesis of UDPG from UMP (U-5'-MP). This is a chemical process using dicyclohexyl carbodiimide (DCC) to esterify UMP to yield UDPG. Another chemical process for UDPG by Bergmeyer et al. is shown in U.S. Pat. No. 3,803,125 where UDPG (examples 4–6) is formed from U-5'-MP amidate ester compounds.

U.S. Pat. No. 3,725,201 to Sugimori et al. describes the process of obtaining UDPG by yeast action from U-5'-MP and glucose. (bottom Col. 2—top Col. 3). U.S. Pat. No. 3,717,547 to Nakayama et al. describes a bacterial fermentation process for production of UDPG from orotic acid or uracil.

5-phosphoribosyl pyrophosphate (PRPP) is a necessary metabolic intermediate in the synthesis of purine and pyrimidine nucleotides as well as other important molecules. Perturbation of the intracellular level of PRPP has been found to be relevant to the origin of certain metabolic diseases (Balis M. E., (1976) Adv. Clin. Chem. 18:213; Kelley, W. N., (1974) A. Meister, ed. 14:1). The inhibitory activity of several antimetabolites requires reaction with PRPP and therapeutic efficacy may depend on the level of PRPP in target cells relative to normal host tissues (Higuchi, T., et al. (1976) Cancer Res. 36:3779; Danks, M. K. et al. (1979) Biochem. Pharmacol. 28:2733). Higuchi et al, supra show PRPP availability to convert the anti-carcinogenic purine drug 6-MP to IMP.

U.S. Pat. No. 4,297,347 of Katsunuma shows 3'-polyphosphate pyrimidine nucleoside activity against leukemia in mice. U.S. Pat. No. 4,141,972 of Nishino et al. deals with mixed 5' and 3' (2') phosphates of purine nucleosides with anti-leukemic activity in mice.

Ardalan et al. in Biochem Pharm 31:1509 (1982) show an increase in PRPP levels in tumor-bearing animals given certain L-glutamine antagonist drugs-DON, azaserine and AT-125 [6-diazo-5-oxo-L-norleucine (DON)]. Also, 5-FU is reported therein as active in combination with methotrexate (P1513) and therefore DON, and AT-125 could be used instead of methotrexate in combination with 5'FU to increase the PRPP pool and direct 5-RU to nucleotides.

PRPP is formed by the interaction of ATP and ribose 5-phosphate (R-5-P) catalyzed by the enzyme PRPP synthetase. R-5-P is related to glucose metabolism by the pentose phosphate shunt. Alteration in glucose metabolism, as seen in glycogen storage disease Type I, has been found to increase the PRPP level in affected cells (Kelley, W. N. et al. (1974) Supra). Methylene blue stimulates the oxidative pentose phosphate pathway and concurrently increases the PRPP availability in chick liver slices (Lipstein, B., et al. (1984) Biochim. Biophys. Acta. 521:45). These findings seem to suggest that R-5-P concentrations is not saturating for intracellular PRPP production and the availability PRPP is directly related to purine synthesis.

UDPG is known to have multiple effects on intrahepatic bilirubin metabolism which in turn are related to the glycogen synthesis occurring in the liver (Casciarri, I. et al. (1977) Accademia Medica Lombarda 32:223). The precise mechanism of these interactions is not clearly defined, but it is believed that UDPG is involved in the induction of various enzymes including some active in carbohydrate metabolism (Okolicsanyi, L., et al. (1973) Enzyme 14:366). PRPP occupies an essential role in intermediary metabolism. It is required in the purine and pyrimidine biosynthetic and recycling pathways. PRPP is formed in cells by the reaction of ATP and ribose-5-phosphate by the catalytic action of PRPP synthetase. Perturbation of the level of PRPP in cells has been found to be related to many severe metabolic disturbances including Glycogen Storage Disease Type I (Balis, M. E., (1976) Adv. Clin. Chem. 18:213; Kelley, W. N., (1974) A. Meister, ed. 14:1).

SUMMARY

The present invention determines that uridine diphosphoglucose (UDPG) exerts an effect on PRPP availability in specific cells for example, tumor cells either by action on cell membranes or by incorporation per se into the cytoplasm. Therapeutic potential of such effects is shown.

BRIEF DESCRIPTION OF THE DRAWING

FIG. 1 is a plot following uptake of $^3$H-UDPG into liver cells at 10, 30 and 40 minutes.

DESCRIPTION

Thus, the present invention contemplates the use of UDPG alone, or preferably in combination with known anti-cancer drugs, preferably of the class of compounds which deplete the purine and pyrimidine pool, to treat tumors in mammals. The types of tumors to be treated, especially in humans, would include tumors of the lung, colon, rectum, breast, prostate, ovaries, head and neck, bone, pancreas, liver, kidney, stomach, bladder and genitalia, and melanomas, soft tissue sarcomas, lymphomas and leukemias.

The UDPG could be administered alone or in combination with other anti-cancer drugs, in single or multiple dosages, by the parenteral (I.V. or I.M.) route. In normal formulations, the UDPG when administered orally will tend to break down in the stomach. Special formulations might be developed which would prevent such UDPG decomposition, and in that event, such UDPG containing special formulations could be administered by the oral route.

The UDPG will be administered to the patient in the amount of 1 to about 300 mg per kg of body weight per day, preferably about 50 to 200 mg per kg per day, and most preferably about 100 mg per kg per day. The higher dosage levels of UDPG, such as in the range of 100 to 300 mg per kg per day, would normally be given by continuous infusion. The inhibition of PRPP synthesis per se is believed to be toxic to tumors, so that the UDPG could be administered alone to inhibit tumors. However, it is most preferred that the UDPG be administered together with an anti-tumor compound which is an inhibitor of purine synthesis, pyrimidine synthesis, or glutamine metabolism. These other anti-tumor drugs can be administered in combination with the UDPG, or in a sequential fashion with the UDPG.

The purine synthesis inhibitors can be antifolates in general, and especially methotrexate. The methotrexate or other antifolate would be administered in conventional amounts, using conventional methods of administration, such as, for instance, an IV administration once a week of from 4 to 400 mg/kg per single weekly dose, or in corresponding lesser daily amounts. Normally, the dose would be monitored by following the serum methotrexate level. It is known to use a rescue technique when methotrexate is administered in the treatment of tumors, and it is contemplated that such a rescue technique would be used if UDPG and methotrexate were administered, for instance, in an amount of 1 gm per sq. meter of patient body surface per 24 hour period, plus serine in an amount of 100 to 300 mg/day in divided doses, and a purine (such as for instance, hypoxanthine in an amount of about 300 and 1500 mg per day in divided doses, and allopurinol at 200 to 400 mg/day in divided doses), or other known rescue agent could be used.

It is known that inhibitors of glutamine metabolism also block purine synthesis, as glutamine is a precursor to purine. Glutamine metabolism is inhibited by azaserine, 6-diazo-5-oxo-L-norleucine (DON), and other compounds and it is contemplated that these glutamine synthesis inhibitors could also be administered with UDPG, with the glutamine synthesis inhibitor being administered in conventional methods of administration and in conventional amounts, such as, for instance, 5 to 15 mg/kg/day, for 2 to 10 days for DON, either alone or sequentially with the UDPG. It would normally be preferred to use a rescue technique with glutamine synthesis inhibitors and the rescue would be with the purine rescue agents described hereinabove.

Inhibitors of pyrimidine synthesis include inhibitors of aspartate transcarbamylase such as N(phosphonacetyl)-L-aspartte (PALA), orotidylate decarboxylase such as pyrazafurin, dihydroorotase of reasonably potent compounds become available and general depletors of available cellular pyrimidine pools such as galactosamine. The pyrimidine synthesis inhibitors are usually used in conjunction with a rescue technique, analogous to that for purine synthesis, with uracil or cytosine being the rescue compound. The rescue compound and the pyrimidine synthesis inhibitor are administered by conventional methods of administration and conventional amounts. For instance, the PALA pyrimidine synthesis inhibitor can be administered in amounts of 0.25 to 5 g/m2/day by injection and pyrazafurin can be administered by I.V. in a single dose of 1–300 mg/m$^2$, or by infusion at a dose of say 250 mg/day for 1–6 days, and the cytosine rescue compound in amounts of 5 to 100 mg/kg/day by infusion, and for uracil approximately 3 to 50 mg/kg/day by infusion.

As will be apparent from the above, the presence of UDPG in the body of a patient having a tumor decreases the PRPP levels in the tumor cells. At the same time, the presence of UDPG maintains or increases the PRPP levels in normal living cells, so that the use of UDPG assists in the specificity of treatment of the tumor cells as opposed to the normal living cells. The average size of the tumor is decreased after prolonged treatment with high dosages of the drug UDPG. The reduction of the mass of the tumor in test animals after treatment with UDPG suggests that the lifespan of the treated animals be prolonged, which in turn suggests that the life of human tumor patients could be correspondingly prolonged.

The dual action of UDPG, which decreased the PRPP level in tumor cells while increasing or at least maintaining the PRPP levels in non-tumor normal cells, even if these normal cells are damaged, is of considerable therapeutic relevance. The dualistic behavior of UDPG may favor the susceptibility of the tumor cells to the action of the antimetabolites and/or other antineoplastic agents, while at the same time, exerting a protective effect on the normal cells of the tumor patient. The selective decrease of PRPP in the tumor cells induced by the drug UDPG, makes these tumor cells more accessible to anti-tumor agents, while at the same time, protecting the other cells of the mammal from the action of the same anti-tumoral agents.

As will be clear from the therapeutic viewpoint, an immediate and approximate result of the above could be not only better efficacy of the antineoplastic treatment, but also a reduction of the cumulative dosage level of co-administered anti-tumor agents. It is therefore believed that the relevant discoveries of the present invention include the following:

a. Director anti-tumor effect of UDPG when administered at various doses.

b. More efficacy of known anti-tumor agents when co-administered with UDPG.

c. Reduction of the side effects of the known anti-tumor agents when administered with UDPG.

d. Better tolerability and drastic decrease of the toxic effects of known anti-tumor agents when co-administered with UDPG.

The prior use of UDPG acknowledged above has been in the treatment of chronic and acute hepatitis, the hyperbilirubinemia and as adjuvant in the hepatic detoxication processes. The administration has been by the parenteral route (I.V. or I.M.) and the daily dosages has varied from 50 to 3–500 mg. Thus, it will be noted that the prior use of UDPG has been at a generally lower daily dosage level than contemplated for the treatment of tumors described herein, as it is generally preferred to administer UDPG in an amount of at least 2000 mg per day in the treatment of tumors. Also, of course, in the prior use of UDPG to treat liver diseases, inhibitors of purine synthesis, pyrimidine synthesis or glutamine metabolism would not be administered. Furthermore, the prior use of UDPG in the treatment of liver diseases has not involved administration by the oral route. Thus, in addition to the method of treatment, the present invention generally contemplates significantly different pharmaceutical compositions to be used for the treatment of tumors.

Based on the test data obtained to date, which data is reported above, it is believed that the best mode of the present invention would be the use of UDPG in an amount of about 100 mg per kg per day, combined with the administration of methotrexate, followed by a purine synthesis rescue technique using thymidine, serine and a purine.

EXPERIMENTAL METHODS

Infusion of UDPG: Mice of various strains, Balb/C, CD$_8$, CRF with and without tumor implants, maintained on Purina rat chow and tap water, were infused intraperitoneally as described previously, (Yip, L. C., et al. (1984) Biochem. Pharmacol. 29:2888) with a phosphate-buffered saline solution of UDPG at a constant rate of 0.8 mg/day for five days. Two concentrations of UDPG were used; 8 mM and 80 mM. Control mice received only buffered saline solution.

After the five-day infusion, the mice were killed, their tissues excised and homogenized in cold PBS solution (1.5 ml per gram tissue) to extract PRPP. The homogenates were centrifuged at 48,000×g for 10 minutes. Supernatants thus prepared were assayed for PRPP and enzyme activity. Pellets were re-suspended in the original volume of 10 mM Tris buffer (pH 7.4), 0.125M sucrose, 1 mM DTT and 2% Triton. The supernatants from the second extraction were used for the assay of membrane-bound PRPP synthetase.

Isolation of splenocytes and hepatic cells: The organs were gently teased apart with forceps over a fine tea strainer into PBS or minimum essential culture medium (MEM) containing 0.1M potassium phosphate buffer pH 7.4 with and without added effectors. The cells were incubated at 37° for 30 minutes and then washed once with PBS before they were lysed in PBS by freezing and thawing three times. The supernatant solutions were assayed for PRPP.

Determination of PRPP concentration; The PRPP was determined through the reaction of $^{14}$C-orotic acid with PRPP to form $^{14}$C-carboxyl orotidine-5'-phosphate in the presence of orotate phosphoribosyl transferase followed by the liberation of $^{14}CO_2$ under the catalysis by OMP decarboxylase (Tax, W. J. M., et al. (1977) Clin. Chim. Acta 78:209). The reaction mixture (100 microliters) contained 25 microliters of 0.1M Tris-HCl (pH 7.4), 25 microliters of enzyme mix (Sigma, St. Louis, Mo. containing 2–3 units/ml in Tris buffer), 25 microliters 0.5 mM $^{14}$C-carboxyl orotic acid (5 mCi/mmole), 25 microliters of 40 mM $MgCl_2$ solution and 25 microliters of clarified tissue homogenate. The test tubes containing the reaction mixture were sealed with serum caps, each of which has suspended from it a plastic well (Kontes Vineland N.J.) containing 200 microliters of protosol (New England Nuclear, Boston, Mass.). The tubes were incubated at 37° for 10 minutes before they were placed in an ice bath and 0.25 ml of 10% TCA was injected through the serum cap. Tubes were returned to a 37° water bath and incubated for one hour. At the end of this time, the tubes were uncapped, the outsides of the wells wiped clean and the suspended wells cut. The wells were placed in scintillation vials and 10 ml of counting cocktail added. The vials were shaken vigorously and their radioactivity determined.

Enzyme assays: PRPP synthetase was assayed as described previously (Yip, L. C., et al. (1980) Am. J. Physiol. 239:G266). The assay is based on the coupling of the PRPP assay using $^{14}$C-adenine with APRTase to form $^{14}$C-AMP with the synthetase reaction (in the presence of ATP and R-5-P).

Protein determination: Protein concentrations were determined by the method of Lowry, et al. (Lowry, O. H., et al. (1951) Biol. Chem. 193:265).

Adenine incorporation studies: Isolated balb/c mouse splenocytes and hepatocytes were incubated at 37° C. in MEM with 0.1M KPB (pH 7.4) and 0.5 mM $^{14}$C-adenine (specific activity 5 Ci/mole) with and without 10 mM UDPG. After 30 minutes of incubation, cells were washed once with PBS before they were lysed in PBS by alternate freezing and thawing (3×). The $^{14}$C-nucleotides thus formed were assayed by chromatography on DEAE-cellulose paper and subsequent assay of the radioactivity.

$^3$H-UDPG incorporation Studies: Isolated mouse hepatocytes were incubated at 37° C. in PBS and MEM containing 0.5 mM UDPG, including 0.21 mM $^3$H-UDPG. After 30 minutes, the cells were layered on top of 1.0 ml of dibenzylamine and centrifuged at 4° immediately to separate the cells from the incubation medium. The cells were lysed in 0.2 ml of KPB (pH 7.4) by vigorous vortexing. The solution was clarified by centrifugation at 30,000×g for 15 minutes, and 25 microliters of 10% TCA were added to 0.1 ml of supernatant solution. The initial pellet (containing cell membranes) was solubilized in 2% Triton in 10 mM Tris (pH 7.4) buffer and deproteinized. Solubilized membranae and cytoplasm preparations were analyzed for $^3$H-containing components by HPLC fractionation through a PXS-102SAX column with a linear gradient from 0.007M $KH_2PO_4$ to 0.25M $KH_2PO_4$, 0.5M KCl (pH4.5). The flow rate was 0.8 ml/minute and fractions were 0.4 ml each. The uv absorption and the radioactivity profiles were compared to values of known standards. The radioactivities of the fractions were determined by liquid scintillation counting.

The following examples are for illustrative purposes only and are not meant to limit the invention to the specific examples shown.

EXAMPLE I

Changes in PRPP levels and PRPP synthetase of Balb/c mouse liver and spleen upon UDPG treatment: Table I shows that treatment with UDPG increased amount of UDPG found in the liver of Balb/c mice. Lower UDPG concentration, introduced by injection of 0.5 ml of 2 mg/ml of UDPG per day caused only a 13% increase of liver PRPP. At slightly higher dose level produced by continuous infusion a 3.3 fold increase in PRPP level was observed. Contrary to expectation, a 10 fold increase in UDPG concentration gave only a 19% increase in PRPP level. The changes in liver PRPP synthetase activity did not correspond well with that observed with its reaction product. The 30–37% increase of the enzyme activity at low dosage UDPG treatment was diminished when the higher concentration of UDPG was used. Mouse spleen was shown to be less sensitive to the UDPG effect. No change in either PRPP or synthetase level was seen at low UDPG concentration. A slight (about 30%) increase in PRPP and synthetase in the cytosol was noted when 80 mM UDPG was infused. UDPG was found to have no effect on PRPP synthetase activity when it was added to the reaction mixture at concentrations up to 10 mM.

EXAMPLE II

Effects of UDPG and G-6-P on splenocyte PRPP level: Isolated splenocytes incubated in media containing various amounts of UDPG or G-6-P were observed to have an increased intracellular PRPP level (Table II). However, the effect of G-6-P was not evident below a concentration of 5.5 mM, while UDPG effect was essentially maximal at 0.7 mM. The effect of G-6-P increased with concentration up to 22 mM while at the highest concentration of UDPG used (14.4 mM), the effect of UDPG appeared to begin to decrease.

EXAMPLE III

Effects of UDPG on tumor-bearing mice: Mammary tumor-bearing $CD_8$ mice and CRF mice with transplanted colon tumors were infused with UDPG for 5 days. At the end of the treatment, the tumors were excised and their weight and the level of PRPP and PRPP synthetase were determined. In one set of experiments, the average size of the mammary tumors was 50% of the controls. The decrease although not statistically significant was determined after only five days of treatment. Nevertheless, the effect is suggestive of possible specificity as is the decrease in tumor level of PRPP compared to the essentially unchanged levels in the host mice (Table III). In a similar experiment (Table IV), PRPP levels of two other proliferating tissues, bone marrow and intestinal mucosa, were also assayed. Although there was a decrease in colonic and bone marrow cells, it was much less then that observed in the tumors. The low values seen in the small bowel may be related to the very high phosphatase level found in this tissue.

EXAMPLE IV

Studies on the incorporation in vitro of $^{14}$C-adenine into splenocytes: Incorporation of adenine into isolated splenocytes was stimulated by the presence of 10 mM UDPG in the incubation medium (Table 5). This result is consistent with the observation (Table II) that UDPG increased the level of PRPP. The PRPP participates in the retention of purine bases by phosphoribosylation of the aglycone (Wohlhueter, R. M., et al. (1982) J.B.C. 257:2691).

EXAMPLE V

Studies on the incorporation in vitro of UDPG into hepatocytes: A study of the transport of tritiated UDPG into liver cells was done at three time periods; 10, 30 and 40 minutes. The cells were prepared as single cell suspensions under conditions that left them viable in terms of several biochemical parameters and vital dye exclusion.

The enclosed plot (FIG. 1) shows the fraction of the material in each of the three compounds that were derived from the glucose moiety of the UDPG. Fractions 11–15 are glucose, fractions 32–36 are glucose monophosphate, and fractions 41–46 are UDPG.

As can be seen there is an uptake of intact UDPG which is maximal at thirty minutes. By forty minutes, the cells have begun to die in this medium and the UDPG has broken down. At thirty minutes about ⅙ of the label is as UDPG. Thus, it is quite apparent that a major amount of the UDPG enters the cells intact. The data further shows that the initial product is glucose phosphate which in time is dephosphorylated to glucose.

It is obvious that the UDPG does not break down before entering the cell both from its presence intact but also from the fact that the breakdown products do not cause the same metabolic response that UDPG does.

Other preliminary studies show the presence of some intact UDPG in the cell membranes. This suggests that there may be an active transport mechanism responsible for the entry of UDPG into the hepatic cell.

The result presented here indicate that the intracellular level of PRPP in animal tissues is greatly affected by the extracellular presence of UDPG. The resulting alteration of PRPP level by UDPG is not linearly dose-related. When higher concentrations of UDPG were used in vivo, a maximal value was reached and concentrations beyond this had a negative effect. The changes in PRPP that were induced by UDPG were also tissue-specific, mouse liver was more sensitive than was the spleen. This latter specificity may well be related to the therapeutically beneficial effects of UDPG.

Our data on the permeability of cell membranes to UDPG, indicate that a significant amount (about 20%) of the UDPG, even though it is a highly polar compound, does readily pass through the membrane unchanged. A large fraction of the UDPG added to incubation media, however is found in the cell as glucose phosphate, indicating cleavage by membrane-bound UDPG phosphatases after penetration of the cell. Eventually, the UDPG that entered the cells was degraded to glucose phosphate and glucose. The in vitro studies show that G-6-P is not the active form and several tests show that uridine does not lead to changes like those seen with UDPG (Bossa, R., et al. (1975) Biochem. 3:531; Pinelli, A., et al. (1976) Biochem. Pharm 25:623; Pinelli, A., et al. (1981) IN: Alcuni Aspetti Fisiopatolieis Diagnostici e Terapeutici in Epatologia. Pacini Ced. P. 121–128). Thus, the most likely mechanism of action is through the membrane. The effects of UDPG on cell metabolism do not appear to be limited to enzyme induction. Others have reported that UDPG can have effects under conditions that bar enzyme induction (Chiesara, E., et al. (1980) Rivistadi Farmacologia e Terapia XI, 103–111).

Since PRPP is involved in many metabolic pathways, changes in intracellular PRPP levels are often not accompanied by obvious changes in the synthetase. PRPP synthetase has been shown to in many respects to be a self-regulating enzyme (Becker, M. A., et al. (1977) J. Biol. Chem. 252:3911). Its activity can be controlled by further aggregation or dissociation of molecular aggregates (Becker, M. A., et al. (1977) J. Biol. Chem. 252:3911, ip, L. C., et al. (1978) Biochem. 17:3286). This phenomenon may explain some of the observations reported here and also suggests that the effect of UDPG on PRPP levels is most likely not due to the induction of additional synthesis of the enzyme, but to alteration of the conformation of the enzyme and the expression of this in a different catalytic function of the synthetase. Under the assay conditions employed, it is quite possible that these differences are masked. This line of reasoning is consistent with the rapid increase in PRPP seen in splenocytes following incubation in medium containing UDPG.

Glucose-6-phosphate can easily be converted intracellularly into ribose-5-phosphate and thus activate the production of PRPP. However, the different effects that we have observed between the G-6-P and UDPG incubation indicates that the UDPG action is not due solely to its increase in intracellular glucose concentration.

Contrary to the effect of UDPG on normal cells, UDPG was seen to decrease PRPP concentration in tumor cells. Since with tumor cells only one very high UDPG concentration was studied it is difficult to assert that the reverse effect is due to the specific sensitivity of the tumor, as was noted between liver and spleen, or due to the nature of the tumor cell membrane. Nevertheless, other rapidly proliferating tissues were also affected albeit less so. Others have reported different changes in PRPP pool sizes in tumors and gut (Ardalan, B., et al. (1982) Biochem. Pharmacol. 31:1509). These observation plus the fact that the weights of the mammary tumor were actually decreased after only five days of exposure to UDPG suggest UDPG as a therapeutic agent especially in combination with inhibitors of the PRPP utilizing steps in purine and pyrimidine synthesis.

TABLE I

CHANGES IN PRPP LEVEL AND PRPP SYNTHETASE AFTER UDPG TREATMENT

| | PRPP | | PS | |
|---|---|---|---|---|
| | C | T | C | T |
| LIVER | | | | |
| Inject 1 mg/day | 206 ± 58 | 233 ± 20 | 4.7 ± 18 | 6.5 ± 3.5 |
| Infuse 4 mg/day | 237 ± 95 | 772 ± 54 | 4.6 ± 1.6 | 6.0 ± 1.6 |
| Infuse 40 mg/day | 276 ± 12 | 328 ± 43 | 4.5 ± 0.4 | 4.4 ± 0.6 |
| SPLEEN | | | | |
| Infuse 4 mg/day | 242 ± 60 | 213 ± 32 | 7.7 ± 0.5 | 7.4 ± 3.7 |
| Infuse 40 mg/day | 228 ± 32 | 302 ± 27 | 7.6 ± 0.8 | 9.4 ± 1.4 |

Balb/c mice were used. C = control, T = treated animals. Control mice received injections or infusions of PBS.

TABLE II

EFFECTS OF UDPG AND G-6-P ON PRPP LEVELS OF ISOLATED SPLENOCYTES

| Concentration of drugs (mM) | | PRPP levels pmoles/mg protein |
|---|---|---|
| G-6-P | 0 | 981 |
|  | 1.1 | 969 |
|  | 5.5 | 1418 |
|  | 11 | 1510 |
|  | 22 | 1998 |
| UDPG | 0 | 981 |
|  | 0.7 | 1825 |
|  | 3.6 | 1937 |
|  | 7.2 | 2135 |
|  | 14.4 | 1508 |

Cells were incubated in vitro in MEM containing indicated compound. Assays were performed on soluble fraction of homogenates.

TABLE III

EFFECTS OF UDPG ON TUMOR-BEARING MICE

|  | LIVER | | SPLEEN | | TUMOR | |
|---|---|---|---|---|---|---|
|  | Cntr | Tr | Cntr | Tr | Cntr | Tr |
| MAMMARY CARCINOMA IN CD$_8$ MICE | | | | | | |
| PRPP nmoles per g protein | 153.08 | 119.58 | 100.37 | 127.16 | 1322.57 | 319.85 |
| SYNTHE-TASE I.U. in lysate | 4.32 | 3.81 | 1.34 | 1.17 | 2.25 | 1.56 |
| SYNTHE-TASE I.U. in membrane | 1.54 | 1.19 | 2.15 | 2.12 | 1.56 | 1.22 |
| COLON TUMOR IN CRF MICE | | | | | | |
| PRPP nmoles per g protein | 213.75 | 218.16 | 176.7 | 197.92 | 1116.83 | 625.56 |
| SYNTHE-TASE I.U. in lysate | 4.8 | 4.58 | 8.43 | 6.72 | 6.76 | 5.77 |
| SYNTHE-TASE I.U. in membrane | 1.32 | 1.37 | 4.60 | 4.18 | 2.25 | 2.51 |

Tr = UDPG infused, Cntr = Saline infused controls

TABLE IV

EFFECT OF UDPG ON PRPP LEVELS OF TISSUES OF TUMOR BEARING MICE

| TISSUE | CONTROL | TREATED |
|---|---|---|
| Tumor | 1704 | 385 |
| Colon | 230 | 112 |
| Jejunum | 20 | 49 |
| Bone Marrow | 131 | 82 |

Mice were CD$_8$ carrying second generation mammary tumors.

TABLE V

EFFECT OF UDPG ON THE INCORPORATION OF $^{14}$C-AD INTO SPLEEN AND LIVER CELLS

|  | $^{14}$C-AMP FORMED pmoles/mg protein/minute |
|---|---|
| Hepatocytes in PBS | 93 |
| Hepatocytes in 10 mM UDPG | 139 |
| Splenocytes in PBS | 76 |
| Splenocytes in 10 mM UDPG | 204 |

I claim:

1. A method of affecting the intracellular PRPP pool size which comprises exposing normal or tumor cells to pharmacologically active levels of UDPG.

* * * * *